United States Patent
Corby

Patent Number: 5,443,849
Date of Patent: * Aug. 22, 1995

[54] SPORICIDAL DISINFECTANT COMPOSITIONS, PRODUCTION AND USE THEREOF

[75] Inventor: Michael P. Corby, Ravenshead, England

[73] Assignee: Diversey Corporation, Mississauga, Canada

[*] Notice: The portion of the term of this patent subsequent to Apr. 18, 2006 has been disclaimed.

[21] Appl. No.: 932,077

[22] Filed: Aug. 19, 1992

[30] Foreign Application Priority Data

Aug. 21, 1991 [GB] United Kingdom ............. 9118000

[51] Int. Cl.⁶ ............... A01N 59/12; A01N 59/00
[52] U.S. Cl. .................................. 424/667; 424/723; 252/106; 252/101; 252/142; 252/187.1; 252/187.2
[58] Field of Search .............. 252/106, 100, 101, 142, 252/146, 187.1, 187.2; 424/723, 667

[56] References Cited

U.S. PATENT DOCUMENTS

| | | | |
|---|---|---|---|
| 2,826,528 | 3/1958 | Shelanski et al. | 167/17 |
| 2,868,686 | 1/1959 | Shelanski et al. | 167/17 |
| 4,131,556 | 12/1978 | Kloptek et al. | 424/723 |
| 4,444,756 | 4/1984 | Schlussler et al. | 424/150 |
| 4,822,513 | 4/1989 | Colby | 252/106 |
| 5,047,164 | 9/1991 | Corby | 252/106 |

FOREIGN PATENT DOCUMENTS 0184904 11/1985 European Pat. Off. .

OTHER PUBLICATIONS

English translation of Russian article by G. V. Keirytkin and A. A. Rozov, entitled "Disinfecting Properties of Some of Polyhaloid Compounds". Published in Trudy Vsesoyvznyi Nauchno—issledovatel'skii Institut Veterinarnoi Sanitarii 1969 (32), pp. 282–285.

Primary Examiner—Marianne M. Cintins
Assistant Examiner—K. Weddington
Attorney, Agent, or Firm—Weintraub, DuRoss & Brady

[57] ABSTRACT

A sporicidal composition characterized in that it comprises iodine bromide in aqueous solution at a pH of less than 7.0

8 Claims, No Drawings

SPORICIDAL DISINFECTANT COMPOSITIONS, PRODUCTION AND USE THEREOF

This invention relates to sporicidal disinfectant compositions, to the production and use thereof; more particularly, it relates to such iodine bromide compositions.

The present invention provides a sporicidal composition characterized in that it comprises iodine bromide in aqueous solution at a pH of less than 7.0.

Generally, the pH of such compositions is between 3.0 and 7.0, preferably between 3.0 and 5.0. The present sporicides may additionally comprise a surfactant, preferably anionic or amphoteric, and/or an emollient and/or an excipient. Naturally, such selections will depend on a variety of known factors, such as the intended application, but should, of course, be halogen-compatible. For example, the sporicidal compositions in accordance with the present invention may be formulated as pre- or post-milking teat dips.

The present invention further provides a process for the production of such a composition characterized in that it comprises reacting a source of iodine with a source of bromine in the presence of an acid selected from nitric acid, phosphoric acid, hydrochloric acid (preferred), sulphamic acid, sulphuric acid or mixtures thereof.

Such production may be direct or indirect, i.e. in one or two stages; the two stage embodiment would generally involve a so-called premix. The pH of the resulting compositon may be adjusted to nearer 7.0 as desired and/or the composition may be diluted prior to use.

The present invention also provides a method for killing spores, in particular anaerobic spores, such as Clostridial spores, characterized in that it comprises the use of such a composition, which may be produced by such a process.

The present invention will now be described more generally.

Certain micro-organisms, in particular the Bacillus and Clostridial species, have the ability in adverse circumstances to devolve into the so-called "spore state". They may exist dormant in this spore form for many years and hence survive some very adverse conditions. Thereafter, when favourable conditions return the spores germinate and re-infect the immediate environment with viable vegetative organisms. For example, spores in milk may survive pasteurization and cheese production processes only to germinate in the finished product causing food spoilage and human health hazard. Bacterial spores are greatly resistant to chemical disinfection.

Some so-called "sporicides" are known, but the possible applications thereof are limited, not only by effectiveness, but also by pH and speed of action, for example. Generally, spores need to be exposed to relatively high concentrations of sporicides for relatively long periods of time, e.g. from 15 to 60 minutes, in order to achieve a useful level of spore population reduction, i.e. a two or three logarithm reduction in viable count. It has now unexpectedly been found that iodine bromide is a particularly attractive, as well as effective sporicide, which does not suffer from the disadvantages of the known examples. Surprisingly, it has been found that spores are particularly sensitive to iodine bromide-based compositions and that such formulations are generally stronger and faster than those hitherto available. By way of illustration, a typical activity in a suspension test technique is a four logarithm reduction in viable spore count in 1 minute and this at a physiologically-acceptable pH, as well as at a lower pH.

Interhalogens are known to be disinfectants and iodine chloride also has limited sporicidal properties. However, the potential uses thereof are severely restricted, particularly, by the necessary low pH. More generally, interhalogens are well known to be unpleasant materials to handle, which are difficult to prepare at all, let alone in widely-usable, commercially-attractive formulations.

Relatively recently, the production of mixed halogen disinfectants from commercially-acceptable ingredients and by a commercially-viable process has been disclosed (U.S. Pat. No. 4,822,513). In fact, this proposal is directed to hard surface disinfectants due to the very low pH, typically below 1.5, which characterises the materials in concentrate form and which is necessary in order to stabilize the active component, in particular iodine chloride in the ionic form $ICl_2$. Such materials have proven very successful both technically and commercially, although they are unavoidably limited to hard surface disinfection as regards field of application.

U.S. Pat. No. 4,822,513 teaches the adjustment to very low pH of alkaline solutions of iodine and iodate, prepared by dissolving elemental iodine in a caustic solution, so as to obtain a stable solution of interhalogen. If such acidic solutions are progressively neutralized, the solution become unstable at a pH which is still too low for applications involving contact with humans or animals. It is possible with some difficulty to raise the pH to about 2.5, but longterm stability problems arise. Surprisingly, in the case of iodine bromide, the formulations are much more tolerant of higher pH, indeed a pH in the human/animal—useful range of 3—7 is perfectly feasible. Such pH adjustment allows a wider field of application and avoids the potential safety hazard of a low pH.

The present iodine bromide compositions offer a significant commercial advantage for human or animal skin application in that no expensive "carrier" is needed to solubilize the active material as is the case with known "iodophor complexes". There may be a further advantage in that common carrier/skin compatibility problems are also avoided. Secondly, they are surprisingly, relatively chemically compatible with organic materials, more specifically with certain emollient systems which are used to promote good skin condition. Most importantly, the use of iodine bromide in accordance with the present invention provides an exceedingly effective sporicidal action, in addition to normal disinfectant properties.

As mentioned above, interhalogens are prepared at low pH. In order to generate the maximum iodine bromide, the reaction is conducted at pH<1.5 and, when the reaction is complete, the pH is raised to the desired pH 3–7 range. If this preferred pH is used for the reaction, the product does not generate the required halogen levels. This post-production pH adjustment is itself surprising as, inter alia, such may not be accomplished with iodine chloride, for example, with respect to chemical stability.

For the first time, products may now be prepared at a pH suitable for use on humans and animals with high levels of available (titratable) halogen and a strong biocidal/sporicidal action, without recourse to a carrier molecule as used in all iodophor products. Iodine is normally soluble in water formulations to about 300 ppm (0.03% w/w) and the carrier molecule increases this solubility to the required concentrate levels between 1000 and 25,000 ppm. Iodine bromide prepared by the present method may, produce up to 25,000 ppm of halogen (expressed as iodine) without recourse to a carrier material. The lack of need for a carrier has a significant effect on the overall cost of such formulations and on the overall acceptability of the whole formulation.

While generally retaining the interhalogen-type of disinfectant activity, the present iodine bromide materials are surprisingly sporicidal and, moreover, are unexpectedly potent and quick-acting. In addition, such materials may be provided at a physiologically-acceptable pH, which is a further significant advantage, if only in that the known disinfectant action is now available at a safer, more attractive pH. As well as the known applications, such as hard surface cleaning, the present invention opens possibilities as regards, for example, hand disinfection for medicinal or food preparation purposes and as antiseptics. With the added advantage of the sporicidal effect, the present compositions are particularly suitable for disinfection of skin and in cleaning in the food processing industry or of surgical instruments. One preferred embodiment of the present invention relates to an advantageous application to animal health and milk hygiene. The iodine bromide-based formulations represent a rapid, simple approach to the pre-milking disinfection of cow teats using less components which might cause contamination of milk supplies and may also represent a valuable cheaper means of providing efficacious post-milking teat dips for mastitis prophylaxis against contagious mastitis.

The following illustrates the present invention:

A premix was prepared as follows:

| Premix A | % w/w |
| --- | --- |
| Water | 92.52 |
| Iodine (elemental) | 2.38 |
| Potassium iodate | 1.10 |
| Caustic soda (50% solution) | 4.00 | high pH solution giving a solution of iodide and iodate. On treatment of this solution with strong acid and chloride ions, the familiar pale yellow solution of $ICl_2-$ is formed after the elemental iodine has redissolved as described in U.S. Pat. No. 4,822,513.

| Example 1 | % w/w |
| --- | --- |
| Premix A | 10.0 |
| Sodium bromide | 2.0 |
| Hydrochloric acid (28%) | 2.0 |
| Phosphoric acid (85%)* | 1.0 |
| Water | Q.S. |

(*The phosphoric acid is optional, but acts as a buffer on neutralization to pH 4.)

The further treatment of the premix as above results in clear orange/brown solutions at pH<1.0. These solutions may, however, be partially neutralized using caustic soda, for example, such that the pH between 3 and 7, typically ~4. The colour of the solution darkens, but nevertheless is remains a stable solution. If only sufficient acid had been added originally to achieve a pH of 3–7, the solutions exhibit available halogen, but they both appear weak in colour and titrate a low level of halogen.

As an example of such a formulation, produced by pH reduction to approximately 0.5, then followed by pH adjustment to approx 4.0, gives:

| Appearance | Dark brown liquid |
| --- | --- |
| Available halogen | 0.5% w/w as $I_2$ |

A further example of such a formulation, neutralized by acid:

| to pH 7 only: | |
| --- | --- |
| Appearance | yellow liquid |
| Available halogen | 0.11% w/w as $I_2$ |
| to pH 5 only: | |
| Appearance | light brown/yellow liquid |
| Available halogen | 0.15% w/w as $I_2$ |
| to pH 3 only: | |
| Appearance | light brown liquid |
| Available halogen | 0.20% w/w as $I_2$ |

Also, it is possible to cycle the pH of these solutions and to titrate available halogen as follows:

| pH adjusted using NAOH or HCl | | Available halogen as $I_2$ % w/w | Appearance |
| --- | --- | --- | --- |
| Add NaOH | 1.0 | 0.51 | Orange |
| | 3.0 | 0.50* | Brown |
| | 6.0 | 0.33 | Light Brown |
| | 7.0 | 0.19 | Straw/yellow |
| | 9.0 | 0.09 | Light straw colour |
| | 11.0 | 0.00 | Water white |
| Add HCl | 7.0 | 0.10 | Pale straw colour |
| | 3.0 | 0.17* | Light Brown |
| | 0.5 | 0.50 | Orange |
| Add NaOH | 3.0 | 0.49* | Brown |
| | 4.0 | 0.49 | Brown |

(*At pH 3, available halogen depends on history.)

Post-milking disinfection of cow teats is generally recognised as useful in preventing the condition known as "parlour" or contagious mastitis. Organisms involved tend to be capable of or even are obligate parasites of the milking cow, e.g. *S. aureus, St. agalactiae* and *St. dysgalactiae*. Other organisms, however, do contaminate a cow's teats and the source of this contamination is the general environment. Such organisms are generally not well controlled by post-milking teat disinfection. The current thinking is that such organisms are deposited on the teats between milkings and then gain entry to the teat/udder system during the actual milking process. Organisms involved in this process, which result in so-called "environmental" mastitis are, e.g. *E. coli, St. uberis* and *Ps. aeruginosa*, as well as many other generally gram-negative species. It has been shown that exposure of the teats to strong disinfectant solutions immediately prior to milking, followed by removal of as much chemical as possible with a paper towel, has a beneficial effect in reducing the incidence of environmental mastitis cases. Typically, the current practice is to dip the cows teats in post-milking teat disinfectants, such as iodophors, for this purpose.

Chemical contamination of the milk supply is, of course, a potential problem with this procedure. It therefore follows that formulation simplicity for such a purpose has merit. Usually, post-milking teat dips contain many ingredients for skin condition, active persistence and rheology modification, for example. In the case of a so-called 'Pre-dip' simplicity is a virtue The formulation of Example 1, for example, has such simplicity.

There is another aspect to pre-milking teat disinfection not associated with post-milking teat disinfection. A cow's teats and udder are preferably and in some cases obligatorily cleaned and disinfected prior to the attachment of the milking machine. Bacterial numbers in the milk supply leaving the farm are of paramount importance to the milk producer as penalty and bonus payments apply to the levels obtained. It is therefore important to the farmer to prepare his cows' teats to give the minimum levels of bacterial contamination in the milk, but also to keep the chemical contamination of the milk to a minimum. Iodine bromide has additional valuable properties to offer in this connection remembering that the polarity of these molecules confers the property of water-solubility, where iodophors require carrier moieties in order to reach efficacious active levels.

The residual ions associated with the use of the formulation of Example 1 will be:

| | | |
|---|---|---|
| Sodium | as | $Na^+$ |
| Potassium | as | $K^+$ |
| Iodide | as | $I^-$ |
| Bromide | as | $Br^-$ |
| Chloride | as | $Cl^-$ |
| and Phosphate | as | $PO_4^{3-}$ |

All of these ions are naturally present in milk in quantities greater than are likely to be associated with residues from the use of the present product. This is not the case with iodophor products, particularly so those originally intended for post-milking teat disinfection. A particular problem associated with the preparation of cows' teats for milking also serves to illustrate the potential effectiveness of the present invention. The spores from certain organisms mentioned above are resistant to normal iodophors and pass into milk leaving the farm. This may cause many problems in cheese manufacture post-pasteurization. For this reason, some milk producers are paid premiums or are subject to penalties on the spore content of ex-farm milk.

Tests evaluating the present formulations for sporicidal effect speak for themselves as to the potential to alleviate this problem at least to some extent.

| Example 2 | % w/w |
|---|---|
| Water | Q.S. |
| NaBr | 2.0 |
| HCl (28%) | 2.0 |
| $H_3PO_4$ (75%) | 1.0 |
| Premix A | 10.0 |
| Caustic Soda | to pH |

The sodium bromide, water and Premix A were mixed. The mixture was acidified using the two acids and, on further mixing, a clear brown solution resulted. The solution was then back-titrated as required using caustic soda.

| Test Protocol | BS 3286 | Suspension test |
|---|---|---|
| | Neutraliser | Thiosulphate |
| | Organisms | *Bacillus cereus* spores |
| | Soil | Absent |
| | Temperature | Ambient |
| | Contact | 1 minute |
| | pH | % kill |

| | |
|---|---|
| 1 | 99.997 |
| 2 | 99.94 |
| 3 | 99.994 |
| 4 | 99.93 |
| 5 | 99.93 |
| 6 | 99.93 |
| 7 | 99.97 |

| Example 3 | % w/w |
|---|---|
| Water | Q.S. |
| Sodium bromide | 2.0 |
| Hydrochloric acid (20%) | 2.0 |
| Phosphoric acid (85%) | 1.0 |
| Premix A | 10.0 |
| Glycerine | 8.0 |
| Caustic soda to pH 4 | |

To most of the water, was added the premix A and the sodium bromide. After dissolution, the hydrochloric acid was added and the colour changed to orange. The phosphoric acid and the glycerine were added and the mixture was stirred until homogenous. The desired pH (4.0) was adjusted by the gradual addition of caustic soda, prior to the addition of the remaining water.

Surprisingly, these formulations are stable both physically and chemically, although there is a slight tendency for the pH to drop in storage.

| Age in weeks Example 3 | pH | Available halogen as % w/w iodine |
|---|---|---|
| 0 | 4.0 | 0.55 |
| 1 | — | 0.55 |
| 2 | — | 0.54 |
| 4 | — | 0.54(5) |
| 6 | 3.6 | 0.54 |
| 11 | 3.6 | 0.53 |
| 18 | 3.6 | 0.51 |

(0.5% w/w halogen is a typical halogen level for mastitis prophylaxis efficacy.)

Such compositions are capable of concentrations similar to iodophor formulations such that the concentrate is capable of dilution.

| Example 4 | % w/w |
|---|---|
| Water | Q.S. |
| Premix A | 50.0 |
| Sodium bromide | 10.0 |
| Hydrochloric acid (28%) | 10.0 |
| Phosphoric acid | 5.0 |
| Glycerine (BP) | 20.0 |
| Caustic soda to pH 4.0 | |

Again, this formulation was prepared by dissolving the sodium bromide in the premix A. The hydrochloric acid was added and the solution turned orange. The phosphoric acid and the glycerine were added and the mixture stirred until homogeneous. The pH was adjusted to 4.0 using caustic soda solution and the remainder of the water added. A formulation prepared as above behaved as follows:

| Age in weeks | pH | Available halogen as % w/w $I_2$ |
|---|---|---|
| 0 | 4.0 | 2.52 |
| 1 | | 2.53 |
| 2 | 3.8 | 2.47 |
| 4 | 3.9 | 2.48 |
| 9 | 3.8 | 2.41 |
| 17 | 3.7 | 2.29 |

The solution is dark brown and clear, free from precipitates.

Because such formulations are actually surface active agent-free (a specific advantage in cost terms), it may be necessary to add small amounts of compatible surface active agents in order to lower the surface tension of solutions in order that they may 'wet' a cow's teat and form an integral film of chemical on the surface.

Hydrobromic acid may also be used as the source of bromide ions.

| Example 5 | % w/w |
|---|---|
| Water | Q.S. |
| Hydrobromic acid (conc) | 2.30 |
| Premix A | 10.0 |
| Glycerine | 10.0 |
| Anionic surfactant (Dowfax 2A1) | 0.1 |
| Caustic soda to pH 4 | |

| Examples 6, 7 and 8 | % w/w |
|---|---|
| Water | Q.S. |
| Premix A | 10.0 |
| Sodium bromide | 2.0 |
| Sulphuric acid (60%)* | 2.0 |
| Caustic soda to pH 4 | |
| *OR Nitric acid (60%) | 2.0 |
| OR Sulphamic acid | 2.0 |

The effectiveness of such formulations in accordance with the present invention may be seen from the following results:

Test A

| Protocol: | BS 3286 | Suspension test |
|---|---|---|
| | Neutralizer | Thiosulphate |
| | Contact | 1 minute |
| | Soil | Absent |
| | Temperature | Ambient |
| Formulation | Organism | Initial count | % Kill |
| Example 3 | S. aureus | $2.7 \times 10^7$ | >99.9996 |
| | E. coli | $3.8 \times 10^7$ | >99.9997 |
| | S. uberis | $3.6 \times 10^7$ | >99.9997 |

Test B

The National Mastitis Council Inc (NMC), of 1840 Wilson Boulevard, Arlington, Va. 22201, USA, has published a test called the "NMC Protocol A Test". This well known and recognized test is a laboratory procedure involving dipping excised cows' teats in bacteria in milk and then the formulation under test. Bacterial number reductions are calculated and the results are used as evidence of the potential efficacy of a teat dip or spray.

Results of an NMC Protocol A Test indicate a high potential for efficacy as a post-milking teat dip/spray.

| Formulation tested | Example 3 | |
|---|---|---|
| Contact time | 10 minutes | |
| Material tested | Organism | Log reduction |
| Deosan Teatcare* PL 5645/4002 | S. uberis | 3.33 |
| 0.4250% Chlorhexidine gluconate | E. coli | 1.86 |
| Deosan Super Excel* PL 5645/4009 | S. uberis | 4.15 |
| 0.5% Iodophor | E. coli | 3.07 |
| Example 3 | S. uberis | 3.94 |
| | E. coli | 2.76 |

(*Both standard products are fully licensed and of proven mastitis prophylactic efficacy.)

The immediate conclusion is that the formulation of Example 3 shows the potential for a full efficacious effect as a post-milking mastitis prophylactic product.

| Test Protocol | BS 3286 | Suspension test |
|---|---|---|
| | Neutralizer | Thiosulphate |
| | Organisms | Bacillus cereus spores |
| | Soil | Absent |
| | Temperature | Ambient |
| | Contact | 1 minute |

| Formulation Tested | ppm Halogen titrated as $I_2$ | Initial count orgs/ml | % Kill |
|---|---|---|---|
| Cidex (glutaraldehyde) activated * | — | $2.0 \times 10^5$ | 90 |
| Hypochlorite solution | 4% w/w available chlorine | $2.9 \times 10^5$ | 82 |
| Iodophor solution | 2500 | $2.9 \times 10^5$ | 85 |
| Iodine monochloride solution at pH 0.5 | 4000 | $1.6 \times 10^4$ | >99.994 |
| Iodine monochloride solution at pH 2.5 | 4000 | $2.0 \times 10^4$ | 93 |
| Iodine bromide dissolved in hydrochloric acid pH 4 | 4000 | $1.6 \times 10^4$ | >99.994 |
| Example 1 | 4000 | $2.0 \times 10^4$ | >99.994 |
| Example 4 75% | 18750 | $1.8 \times 10^5$ | 99.92 |
| Example 4 50% | 12500 | " | 99.91 |
| Example 4 40% | 10000 | " | 99.91 |
| Example 4 30% | 7500 | " | 99.91 |
| Example 4 20% | 5000 | " | 99.9 |
| Example 4 10% | 2500 | " | 99.9 |
| Example 4 5% | 1250 | " | 99.5 |
| Example 4 2.5% | 625 | " | 99.3 |
| Example 4 1.0% | 250 | " | 96 |
| Example 5 | 4000 | $2.0 \times 10^5$ | 99.997 |

(*Cidex is a well known commercially available sporicide)

A further example has been prepared for use as a pre-milking teat dip for dairy cattle. The formulation test is as follows and was prepared without recourse to a premix.

| Example 9 | % w/w |
|---|---|
| Water | Q.S. |
| Iodine | 1.19 |
| Caustic soda (46%) | 2.00 |
| Potassium iodate | 0.55 |
| Sodium bromide | 10.00 |
| Hydrochloric acid | 10.00 |
| Phosphoric acid | 5.00 |
| Caustic soda (46%) | ~7.00 to pH 4 |
| Amphoteric surfactant (Genamin KB2X) | 0.10 |

The mixer was charged with most of the water, the caustic soda, potassium iodate and iodine were added and stirred until dissolved. The sodium bromide was added and dissolved. On addition of the hydrochloric acid and the phosphoric acid, the solution turned brown and the iodine bromide was formed. The solution was then adjusted to pH 4 and a suitable surfactant optionally added. The remaining water was calculated and the batch brought up to 100% w/w.

The specification agreed and used is as follows:

| Halogens as $I_2$ | 2.4% w/w ± 0.08% |
|---|---|
| pH | 4 ± 0.5 |
| Clear brown homogeneous solution | |
| Foams if surfactant has been used. | |

This product has been tested on farms.

A 10% dilution of Example 9 was selected for the first trial because it was felt that, if successful, it would be the most economically viable to the farmer. Table 2.1 below shows the statistically significant results calculated using a paired t-test.

TABLE 2.1

| | | MEAN COUNTS (per ml) | | |
|---|---|---|---|---|
| Microbiological Test | Farm | With predip | Without predip | Statistical Significance (%) |
| Total Bacterial Count | 1+ 2+ 3 | 13.5 × 10³ | 24.8 × 10³ | 90 |
| Anaerobic Spores | 1+ 3 | 12 | 18 | 90 |
| Staphylococcus aureus | 1 + 2 + 3 | 633 | 1065 | 95 |
| Streptococcus faecalis | 1+ 2 | 284 | 676 | 90 |

The 90% statistical significance achieved when the Total Bacterial Counts (TBC) for all the farms are compared (with predip v. without predip) is a valuable result. The average reduction from $24.8 \times 10^3$ (without predip) to $13.5 \times 10^3$ (with predip) means that the TBC has dropped from a Band B to a Band A hygiene level.

The milk price paid by the Milk Marketing Board (MMB, England and Wales) to the farmer currently varies with the bacterial count as follows:

| Band | Average number of bacteria ($\times 10^3$ per ml) | Milk price adjustment (pence per litre) |
|---|---|---|
| A | 20 or less | +0.230 |
| B | above 20 and up to 100 | NIL |
| C | above 100 | −1.500 to −10.000 (depending on frequency) |

*Staphylococcus aureus* was also reduced on all three farms when predip was used during the trial. This could be due to less contact between milkers' hands and the cows' teats when predipping takes place or due to teat skin sanitation. (Usual udder preparation methods require more hand to teat contact which may increase levels of *S. aureus* in the milk).

Levels of anaerobic spores in the milk were low throughout the trial. This may account for the fact that there was no statistical significance of the results for all three farms as Example 9 is a known sporicide. Analysis of the anaerobic spore results for inter-farm comparison did reveal a difference between with predip and without predip on Farms 1 and 3.

*Streptococcus faecalis* levels were significantly different (284 with predip v. 676 without predip) when Farms 1 and 2 were compared together. When the results from Farm 3 were included no statistical significance was observed.

Table 3.1 shows the 20% dilution of Example 9 results which achieved statistical significance.

TABLE 2.1

| | | MEAN COUNTS (per ml) | | |
|---|---|---|---|---|
| Microbiological Test | Farm | With predip | Without predip | Statistical Significance (%) |
| Total Bacterial Count | 1+ 2+ 3 | 14.9 × 10³ | 24.5 × 10³ | 90 |
| Anaerobic Spores | 1+ 2 | 9 | 12 | 95 |
| Staphylococcus aureus | 2+ 3 | 1055 | 1923 | 95 |
| Streptococcus faecalis | 1 + 2+ 3 | 196 | 485 | 99 |

The use of predip has again reduced the Total Bacterial Count (TBC) from a Band B figure ($24.5 \times 10^3$) to a Band A figure ($14.9 \times 10^3$). This would currently lead to a bonus of 0.23 pence per liter in England and Wales.

Although there was an increase in concentration of Example 9 to 20%, there was seemingly no corresponding extra decrease in TBC. This indicates that there would be no extra benefit in using the more concentrated application.

Better results against *Streptococcus faecalis* were obtained in that all three farms together produced a 99% significant result.

The statistically significant result for all three farms achieved against *Staphylococcus aureus* for the 10% dilution was not repeated for the 20% dilution of Example 9. The result for Farms 2 and 3 shows that there is still a potential advantage in using a predip.

There was no improvement in the result for anaerobic spores using a 20% dilution over a 10% dilution, but the result has now shifted to Farms 1 and 3 together rather than 1 and 2 together.

Iodine residues remained unaffected by the increase in Example 9 concentration and all other results were not statistically significant.

The results for the 10% dilution and the 20% dilution of Example 9 are not significantly different and any potential advantage of a higher concentration is not evident from the results.

Statistical analysis (with predip v. without predip) of a combination of all the results from the three farms, for both the 10% dilution and the 20% dilution of Example 9, produced the following statistically significant results for all three farms.

| | MEAN COUNTS (per ml) (n = 24) | | Statistical |
|---|---|---|---|
| Microbiological Test | With predip | Without predip | Significance (%) |
| Total Bacterial Count | 14.4 × 10³ | 24.6 × 10³ | 98 |

-continued

| Microbiological Test | MEAN COUNTS (per ml) (n = 24) | | Statistical Significance (%) |
|---|---|---|---|
| | With predip | Without predip | |
| Anaerobic Spores | 10 | 13 | 90 |
| *Streptococcus faecalis* | 205 | 463 | 99 |

These results were encouraging, particularly with regard to milk hygiene, as they show that an improvement in bacteriological quality is achievable using the Example 9 predip.

All samples of milk were analyzed for iodine (iodide) content using an Ion Selective Electrode (ISE) technique. No statistically significant differences could be found in the ISE results for iodide with and without the use of Example 9 as a predip at all the concentrations used.

I claim:

1. A sporicidal composition comprising:
   iodine bromide in aqueous solution at a pH between 3 and 7, the iodine bromide being such that a used solution from said composition comprises at least 0.1 w/w $I_2$.

2. A composition as claimed in claim 1 wherein the pH is between 3.0 and 5.0.

3. A composition as claimed in claim 1 which additionally comprises a surfactant.

4. A composition as claimed in claim 1 which additionally comprises an emollient.

5. A composition as claimed in claim 1 which additionally comprises an excipient.

6. A composition as claimed in claim 3 wherein the surfactant is anionic.

7. A composition as claimed in claim 3 wherein the surfactant is amphoteric.

8. A composition as claimed in claim 1 wherein it is in the form of a pre- or post-milking teat dip.

* * * * *